(12) United States Patent
Ethelfeld

(10) Patent No.: US 8,740,851 B2
(45) Date of Patent: *Jun. 3, 2014

(54) INTEGRATED PACKAGE

(75) Inventor: Erik Winkel Ethelfeld, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 122 days.

This patent is subject to a terminal disclaimer.

(21) Appl. No.: 12/877,568

(22) Filed: Sep. 8, 2010

(65) Prior Publication Data

US 2011/0060289 A1    Mar. 10, 2011

Related U.S. Application Data

(63) Continuation of application No. 11/266,904, filed on Nov. 4, 2005, now abandoned, which is a continuation of application No. PCT/DK2004/000334, filed on May 10, 2004.

(60) Provisional application No. 60/471,196, filed on May 16, 2003.

(51) Int. Cl.
*A61M 5/32* (2006.01)

(52) U.S. Cl.
USPC .. 604/180; 604/136; 604/164.01; 604/167.01

(58) Field of Classification Search
USPC ........... 604/93.01, 131, 134, 141, 890.1, 264, 604/174, 180, 136, 164.01, 167.01; 206/438, 365, 524.1, 440
See application file for complete search history.

(56) References Cited

U.S. PATENT DOCUMENTS

| 55,711 A | 6/1866 | Regester |
| 69,546 A | 10/1867 | DeFrost |
| 123,740 A | 2/1872 | Stevens |

(Continued)

FOREIGN PATENT DOCUMENTS

| CA | 2239457 | 12/1999 |
| CN | 1612758 | 5/2005 |

(Continued)

OTHER PUBLICATIONS

International Search Report mailed Jul. 5, 2007 in international application No. PCT/EP2007/053923.

(Continued)

*Primary Examiner* — Theodore Stigell
(74) *Attorney, Agent, or Firm* — Wesley A. Nicolas; Marc A. Began; Reza Green

(57) ABSTRACT

The present invention generally relates to skin-mountable devices. A device in accordance with the invention comprises a skin-mountable unit having a mounting surface comprising adhesive for adhering the unit to the skin of a subject, and a handling unit releasably attached to the skin-mountable unit. The handling unit comprises an interior space at least partially accommodating the skin-mountable unit and has an opening through which the skin-mountable unit can be moved when detached from the handling unit, the handling unit having a portion surrounding the opening. A seal member is releasably attached to the circumferential portion, providing a closed space for the skin-mountable unit. The device allows for easy handling. The user can grip the handling unit and handle the combined device during operation. The handling unit can be designed and optimized for ease of use during manipulation of the skin-mountable unit.

21 Claims, 17 Drawing Sheets

(56) References Cited

U.S. PATENT DOCUMENTS

| | | | |
|---|---|---|---|
| 858,001 A | 6/1907 | Howe | |
| 2,605,765 A | 6/1947 | Kollsman | |
| 2,960,097 A | 11/1960 | Scheffler | |
| 2,980,032 A | 4/1961 | Schneider | |
| 3,705,601 A | 12/1972 | Arisland | |
| 4,016,879 A | 4/1977 | Mellor | |
| 4,077,405 A | 3/1978 | Haerten et al. | |
| 4,137,020 A | 1/1979 | Ito et al. | |
| 4,245,634 A | 1/1981 | Albisser et al. | |
| 4,262,824 A | 4/1981 | Hrynewycz | |
| 4,340,048 A | 7/1982 | Eckenhoff | |
| 4,370,305 A | 1/1983 | Affonso | |
| 4,378,015 A | 3/1983 | Wardlaw | |
| 4,399,824 A | 8/1983 | Davidson | |
| 4,402,407 A | 9/1983 | Maly | |
| 4,519,792 A | 5/1985 | Dawe | |
| 4,529,401 A | 7/1985 | Leslie et al. | |
| 4,544,369 A | 10/1985 | Skakoon et al. | |
| 4,552,561 A | 11/1985 | Eckenhoff et al. | |
| 4,645,491 A | 2/1987 | Evans | |
| 4,657,490 A | 4/1987 | Abbott | |
| 4,710,170 A | 12/1987 | Haber | |
| 4,734,092 A | 3/1988 | Millerd | |
| 4,753,651 A | 6/1988 | Eckenhoff | |
| 4,755,173 A | 7/1988 | Konopka et al. | |
| 4,788,556 A | 11/1988 | Hoisington et al. | |
| 4,871,351 A | 10/1989 | Feingold | |
| 4,877,034 A | 10/1989 | Atkins et al. | |
| 4,886,499 A * | 12/1989 | Cirelli et al. | 604/131 |
| 4,894,054 A | 1/1990 | Miskinyar | |
| 4,928,528 A | 5/1990 | Marques | |
| 4,994,078 A | 2/1991 | Jarvik | |
| 5,008,110 A | 4/1991 | Benecke et al. | |
| 5,049,146 A | 9/1991 | Bringham et al. | |
| 5,076,890 A | 12/1991 | Balembois | |
| 5,122,116 A | 6/1992 | Kriesel et al. | |
| 5,122,201 A | 6/1992 | Frazier et al. | |
| 5,149,340 A | 9/1992 | Waycuilis | |
| 5,169,390 A | 12/1992 | Athayde et al. | |
| 5,211,201 A | 5/1993 | Kamen et al. | |
| 5,224,843 A | 7/1993 | van Lintel | |
| 5,256,157 A | 10/1993 | Samiotes et al. | |
| 5,336,052 A | 8/1994 | Zöllner et al. | |
| 5,390,671 A | 2/1995 | Lord et al. | |
| 5,391,950 A | 2/1995 | Krawczak | |
| 5,482,473 A | 1/1996 | Lord et al. | |
| 5,485,917 A | 1/1996 | Early | |
| 5,494,415 A | 2/1996 | Morita | |
| 5,514,095 A | 5/1996 | Brightbill et al. | |
| 5,527,288 A | 6/1996 | Gross et al. | |
| 5,568,806 A | 10/1996 | Cheney, II et al. | |
| 5,584,808 A | 12/1996 | Healy | |
| 5,584,813 A | 12/1996 | Livingston et al. | |
| 5,586,085 A | 12/1996 | Lichte | |
| 5,609,572 A | 3/1997 | Lang | |
| 5,647,853 A | 7/1997 | Feldmann et al. | |
| 5,720,391 A | 2/1998 | Dohm et al. | |
| 5,776,109 A | 7/1998 | Urrutia | |
| 5,814,020 A | 9/1998 | Gross | |
| 5,851,197 A | 12/1998 | Marano et al. | |
| 5,858,001 A | 1/1999 | Tsals et al. | |
| 5,860,952 A | 1/1999 | Quinn | |
| 5,913,856 A | 6/1999 | Chia et al. | |
| 5,925,017 A | 7/1999 | Kriesel et al. | |
| 5,928,194 A | 7/1999 | Maget | |
| 5,931,814 A | 8/1999 | Alex et al. | |
| 5,941,611 A | 8/1999 | Trzmiel et al. | |
| 5,954,643 A | 9/1999 | Van Antwerp et al. | |
| 5,957,895 A | 9/1999 | Sage et al. | |
| 5,968,011 A | 10/1999 | Larsen et al. | |
| 5,997,501 A | 12/1999 | Gross et al. | |
| 6,045,534 A | 4/2000 | Jacobsen et al. | |
| 6,060,319 A | 5/2000 | Deetz et al. | |
| 6,074,369 A | 6/2000 | Sage et al. | |
| 6,083,196 A | 7/2000 | Trautman et al. | |
| 6,088,619 A | 7/2000 | Hein et al. | |
| 6,099,512 A | 8/2000 | Urrutia | |
| 6,120,492 A | 9/2000 | Finch et al. | |
| 6,123,519 A | 9/2000 | Kato et al. | |
| 6,126,637 A | 10/2000 | Kriesel et al. | |
| 6,132,755 A | 10/2000 | Eicher et al. | |
| 6,165,155 A | 12/2000 | Jacobsen et al. | |
| 6,241,704 B1 | 6/2001 | Peterson et al. | |
| 6,270,478 B1 | 8/2001 | Mernøe | |
| 6,280,148 B1 | 8/2001 | Zengerle et al. | |
| 6,293,925 B1 | 9/2001 | Safabash et al. | |
| 6,302,866 B1 | 10/2001 | Marggi | |
| 6,302,869 B1 | 10/2001 | Klitgaard | |
| 6,358,731 B1 | 3/2002 | Hsu | |
| 6,364,865 B1 | 4/2002 | Lavi et al. | |
| 6,485,461 B1 | 11/2002 | Mason et al. | |
| 6,500,150 B1 | 12/2002 | Gross et al. | |
| 6,551,276 B1 | 4/2003 | Mann et al. | |
| 6,554,791 B1 | 4/2003 | Cartledge et al. | |
| 6,555,986 B2 | 4/2003 | Moberg | |
| 6,558,351 B1 | 5/2003 | Steil et al. | |
| 6,589,229 B1 | 7/2003 | Connelly et al. | |
| 6,613,015 B2 | 9/2003 | Sandstrom et al. | |
| 6,622,037 B2 | 9/2003 | Kasano | |
| 6,656,159 B2 | 12/2003 | Flaherty | |
| 6,716,192 B1 | 4/2004 | Orosz | |
| 6,740,059 B2 | 5/2004 | Flaherty | |
| 6,749,587 B2 | 6/2004 | Flaherty | |
| 6,808,691 B1 | 10/2004 | Herve et al. | |
| 6,818,178 B2 | 11/2004 | Kohl et al. | |
| 6,878,136 B2 | 4/2005 | Fleury et al. | |
| 6,949,084 B2 | 9/2005 | Marggi et al. | |
| 6,960,192 B1 | 11/2005 | Flaherty et al. | |
| 7,052,483 B2 | 5/2006 | Wojcik | |
| 7,070,580 B2 | 7/2006 | Nielsen | |
| 7,097,631 B2 | 8/2006 | Trautman et al. | |
| 7,097,690 B2 | 8/2006 | Usher et al. | |
| 7,141,023 B2 | 11/2006 | Diermann et al. | |
| 7,144,384 B2 | 12/2006 | Gorman et al. | |
| 7,303,073 B2 | 12/2007 | Raynal-Olive et al. | |
| 7,744,570 B2 | 6/2010 | Fangrow | |
| 8,029,469 B2 * | 10/2011 | Ethelfeld | 604/136 |
| 2001/0025168 A1 | 9/2001 | Gross et al. | |
| 2002/0040083 A1 | 4/2002 | Kuwaki et al. | |
| 2002/0040208 A1 | 4/2002 | Flaherty et al. | |
| 2002/0055711 A1 | 5/2002 | Lavi et al. | |
| 2002/0064468 A1 | 5/2002 | Wade | |
| 2002/0123740 A1 | 9/2002 | Flaherty et al. | |
| 2002/0161332 A1 | 10/2002 | Ramey | |
| 2002/0169416 A1 | 11/2002 | Gonnelli et al. | |
| 2003/0009131 A1 | 1/2003 | Van Antwerp et al. | |
| 2003/0009133 A1 | 1/2003 | Ramey | |
| 2003/0029501 A1 | 2/2003 | Williamson et al. | |
| 2003/0060781 A1 | 3/2003 | Mogensen et al. | |
| 2003/0065308 A1 | 4/2003 | Lebel et al. | |
| 2003/0069546 A1 | 4/2003 | Sandstrom et al. | |
| 2003/0073952 A1 | 4/2003 | Flaherty et al. | |
| 2003/0088238 A1 | 5/2003 | Poulsen et al. | |
| 2003/0114797 A1 | 6/2003 | Vaillancourt et al. | |
| 2003/0135159 A1 | 7/2003 | Daily et al. | |
| 2003/0167035 A1 | 9/2003 | Flaherty et al. | |
| 2003/0187395 A1 | 10/2003 | Gabel et al. | |
| 2003/0194328 A1 | 10/2003 | Bryant et al. | |
| 2003/0199823 A1 | 10/2003 | Bobroff et al. | |
| 2003/0216686 A1 | 11/2003 | Lynch et al. | |
| 2003/0236498 A1 | 12/2003 | Gross et al. | |
| 2004/0051674 A1 | 3/2004 | Mahringer | |
| 2004/0087240 A1 | 5/2004 | Chen et al. | |
| 2004/0098068 A1 | 5/2004 | Carbunaru et al. | |
| 2004/0115068 A1 | 6/2004 | Hansen et al. | |
| 2004/0116905 A1 | 6/2004 | Pedersen et al. | |
| 2004/0127844 A1 | 7/2004 | Flaherty | |
| 2004/0158207 A1 | 8/2004 | Hunn et al. | |
| 2004/0162521 A1 | 8/2004 | Bengtsson | |
| 2004/0171403 A1 | 9/2004 | Mikkola | |
| 2004/0199123 A1 | 10/2004 | Nielsen | |
| 2004/0204673 A1 | 10/2004 | Flaherty | |
| 2004/0220497 A1 | 11/2004 | Findley et al. | |
| 2004/0220536 A1 | 11/2004 | VanTassel et al. | |

(56) References Cited

U.S. PATENT DOCUMENTS

| | | |
|---|---|---|
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |
| 2005/0077225 A1 | 4/2005 | Usher et al. |
| 2005/0101933 A1 | 5/2005 | Marrs et al. |
| 2005/0171513 A1 | 8/2005 | Mann et al. |
| 2005/0203461 A1 | 9/2005 | Flaherty et al. |
| 2005/0240154 A1 | 10/2005 | Mogensen et al. |
| 2006/0015063 A1 | 1/2006 | Butikofer et al. |
| 2006/0017576 A1 | 1/2006 | Gordon et al. |
| 2006/0020300 A1 | 1/2006 | Nghiem et al. |
| 2006/0142698 A1 | 6/2006 | Ethelfeld |
| 2006/0200073 A1 | 9/2006 | Radmer et al. |
| 2006/0264835 A1 | 11/2006 | Nielsen et al. |
| 2007/0021733 A1 | 1/2007 | Hansen et al. |
| 2007/0073228 A1 | 3/2007 | Mernoe et al. |
| 2007/0104596 A1 | 5/2007 | Preuthun et al. |
| 2007/0112301 A1 | 5/2007 | Preuthun et al. |
| 2008/0009805 A1 | 1/2008 | Ethelfeld |
| 2009/0163874 A1 | 6/2009 | Krag et al. |

FOREIGN PATENT DOCUMENTS

| | | |
|---|---|---|
| DE | 2552446 | 5/1977 |
| DE | 10255817 | 6/2004 |
| DK | PA 2003 00696 | 5/2003 |
| DK | PA 2003 00697 | 5/2003 |
| EP | 20060277 | 3/1986 |
| EP | 398583 | 11/1990 |
| EP | 568176 | 11/1993 |
| EP | 937475 | 8/1999 |
| EP | 1177802 | 7/2001 |
| EP | 1177802 | 2/2002 |
| EP | 1256356 | 11/2002 |
| EP | 1329233 | 7/2003 |
| EP | 1475113 | 11/2004 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | WO02/005889 | 7/2001 |
| WO | WO 02/02165 | 1/2002 |
| WO | WO 02/04048 | 1/2002 |
| WO | WO 02/15889 | 2/2002 |
| WO | WO02/15965 | 2/2002 |
| WO | WO 02/40083 | 5/2002 |
| WO | WO02/47746 | 6/2002 |
| WO | WO0245574 | 6/2002 |
| WO | WO02/055132 | 7/2002 |
| WO | WO 02/070024 | 9/2002 |
| WO | WO02/081012 | 10/2002 |
| WO | WO02/100457 | 12/2002 |
| WO | WO03000696 | 1/2003 |
| WO | WO03000697 | 1/2003 |
| WO | WO03/026726 | 4/2003 |
| WO | WO03/026728 | 4/2003 |
| WO | WO 03/080169 | 10/2003 |
| WO | WO03/089028 | 10/2003 |
| WO | WO 03/090509 | 11/2003 |
| WO | WO 03/099358 | 12/2003 |
| WO | WO 2004/009160 | 1/2004 |
| WO | WO2004/029457 | 4/2004 |
| WO | WO2004/030728 | 4/2004 |
| WO | WO2004/098682 | 11/2004 |
| WO | WO 2004/098683 | 11/2004 |
| WO | WO2004/098684 | 11/2004 |
| WO | WO 2004/101071 | 11/2004 |
| WO | WO2005/002649 | 1/2005 |
| WO | WO 2005/011779 | 2/2005 |
| WO | WO 2005/025652 | 3/2005 |
| WO | WO2005/037185 | 4/2005 |
| WO | WO2005037350 | 4/2005 |
| WO | WO2005039673 | 5/2005 |
| WO | WO2005/094919 | 10/2005 |
| WO | WO 2005/123186 | 12/2005 |
| WO | WO 2005/123189 | 12/2005 |
| WO | WO2006/060277 | 6/2006 |
| WO | WO 2006/067217 | 6/2006 |
| WO | WO 2006/077263 | 7/2006 |
| WO | WO2006/089958 | 8/2006 |
| WO | WO 2006/120253 | 11/2006 |
| WO | WO 2006/123329 | 11/2006 |
| WO | WO2007/122207 | 11/2007 |
| WO | WO 2009/021950 | 2/2009 |

OTHER PUBLICATIONS

International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977.
JP 2000-513259 Machine Translation, published Oct. 10, 2000, JP 2000-513259.
JP 2000-104659 Machine Translation, published Apr. 11, 2000.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.
Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.

(56) References Cited

OTHER PUBLICATIONS

Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Apl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Notice of Abandonment mailed Oct. 12, 2010 in U.S. Appl. No. 11/266,904, filed Nov. 4, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Final Office Action mailed Sep. 11, 2007 in U.S. Appl. No. 11/266,904, filed Nov. 4, 2005 by Ethelfeld et al.
Non-Final Office Action mailed Jan. 5, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
English Language Machine Translation for JP 2002 505601.
English Language Machine Translation for JP 2000 515394.
Non-Final Rejection Mailed on Mar. 12, 2009 in U.S. Appl. No. 11/250,233, filed Oct. 14, 2005 by Ethelfeld et al.
Final Rejection Mailed on Oct. 16, 2009 in U.S. Appl. No. 11/250,233, filed Oct. 14, 2005 by Ethelfeld et al.
Non-Final Rejection Mailed on Mar. 27, 2007 in U.S. Appl. No. 11/266,905, filed Nov. 4, 2005 by Ethelfeld et al.
Final Rejection Mailed on Oct. 5, 2007 in U.S. Appl. No. 11/266,905, filed Nov. 4, 2005 by Ethelfeld et al.
Non-Final Rejection Mailed on Aug. 25, 2008 in U.S. Appl. No. 11/266,905, filed Nov. 4, 2005 by Ethelfeld et al.
Non-Final Rejection Mailed on Mar. 18, 2009 in U.S. Appl. No. 11/266,905, filed Nov. 4, 2005 by Ethelfeld et al.
Final Rejection Mailed on Oct. 30, 2009 in U.S. Appl. No. 11/266,905, filed Nov. 4, 2005 by Ethelfeld et al.
Non-Final Rejection Mailed on Aug. 19, 2010 in U.S. Appl. No. 11/266,905, filed Nov. 4, 2005 by Ethelfeld et al.
Non-Final Rejection Mailed on Mar. 28, 2008 in U.S. Appl. No. 11/266,821, filed Nov. 4, 2005 by Erik Winkel Ethelfeld.
Final Rejection Mailed on Jul. 18, 2008 in U.S. Appl. No. 11/266,821, filed Nov. 4, 2005 by Erik Winkel Ethelfeld.
Non-Final Rejection Mailed on Jan. 29, 2009 in U.S. Appl. No. 11/266,821, filed Nov. 4, 2005 by Erik Winkel Ethelfeld.
Non-Final Rejection Mailed on Nov. 27, 2009 in U.S. Appl. No. 12/303,307, filed Dec. 3, 2008 by Krag et al.
Final Rejection Mailed on Apr. 16, 2010 in U.S. Appl. No. 12/303,307, filed Dec. 3, 2008 by Krag et al.
Non-Final Rejection Mailed on Apr. 6, 2010 in U.S. Appl. No. 12/298,253, filed Oct. 23, 2008 by Krag et al.
US 6,197,009, 03/2001, Steg (withdrawn)

* cited by examiner

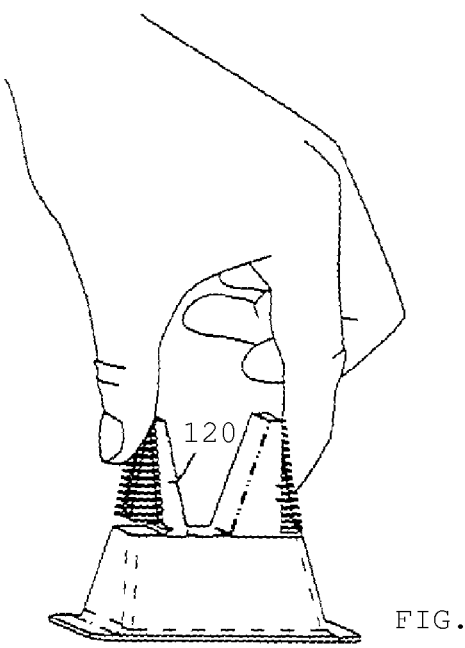
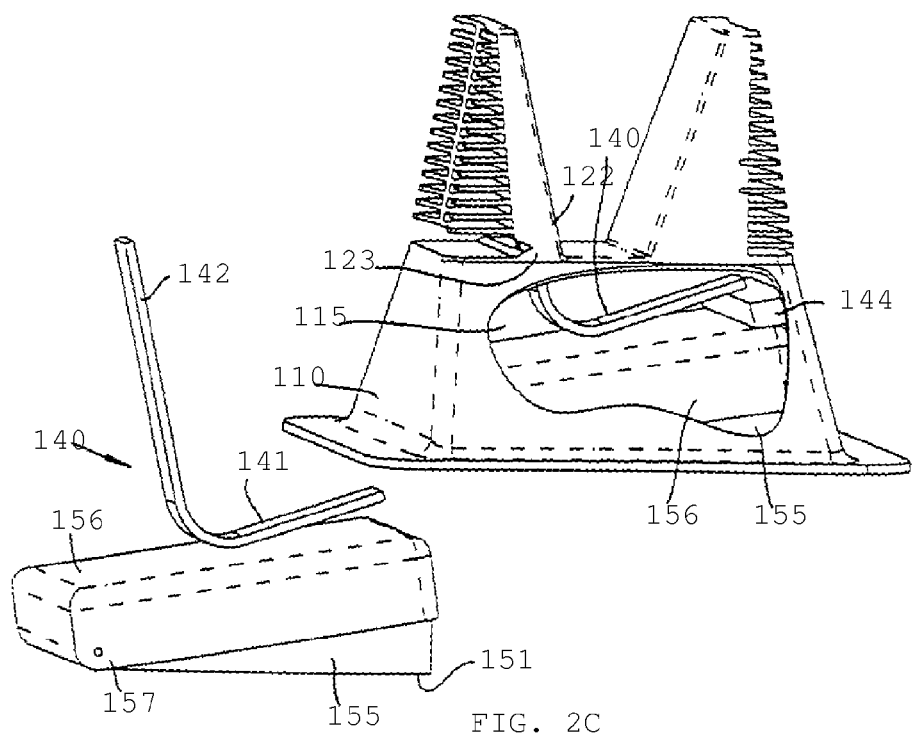

INTEGRATED PACKAGE

CROSS REFERENCE TO RELATED APPLICATIONS

This application is a continuation of U.S. application Ser. No. 11/266,904, filed Nov. 4, 2005, which is a continuation of international application no. PCT/DK2004/000334 filed May 10, 2004 and claims priority of Danish application no. PA 2003 00698 filed May 8, 2003 and U.S. provisional application Ser. No. 60/471,196 filed May 16, 2003, all of which are hereby incorporated by reference.

The present invention generally relates to skin-mountable devices. Especially, the invention relates to such devices which are supplied to the user in a package from which the device has to be removed prior to use.

BACKGROUND OF THE INVENTION

In the disclosure and discussion of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a transcutaneous access device such as a hollow infusion needle, as well as expelling means for expelling a drug out of the reservoir and through the skin of the subject via the hollow needle. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniences, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump), U.S. Pat. No. 5,527,288 (based on a gas generating pump), or US patent (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the user, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. An advantage of this design is that the needle is arranged in a fixed position relative to the reservoir. WO 02/15965 discloses a similar infusion device in which a base plate member acts as a protecting element until an upper part of the device, to which the needle is fixed, is moved down into engagement with the base plate member.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Although the automatic needle insertion means adds convenience for the user and may serve to overcome needle fear, such means also adds to the complexity and bulkiness of the device, the first issue adding to the cost of the device, the latter issue making the device less attractive and convenient to wear.

As the above-described infusion devices all comprise a subcutaneous needle, the devices have to be supplied to the user in a sterile state, i.e. in a sterile package.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a needle-formed sensor element.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391, 950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568, 806.

DISCLOSURE OF THE INVENTION

Having regard to the above-identified problems, it is an object of the present invention to provide a skin-mountable device which can be supplied to the user in a sealed enclosure, which is convenient to handle and use, and which can be manufactured cost effectively.

Thus, in a general aspect a device is provided, comprising a first skin-mountable unit having a mounting surface comprising adhesive means for adhering the unit to the skin of a subject, a second handling unit releasably attached to the skin-mountable unit and comprising an interior space at least partially accommodating the skin-mountable unit and having an opening through which the skin-mountable member can be moved when detached from the handling unit, the handling unit having a portion surrounding the opening, the device further comprising a seal member releasably attached to the surrounding portion, thereby providing a closed space for the skin-mountable unit. By the term partially is defined that a portion of the first unit may project from the opening.

In this way a device is provided allowing for easy handling as a user can use the handling unit to grip and handle the combined device during operation thereof, just as the second unit may be designed and optimized for ease of use during manipulation (e.g. activation) of the skin-mountable unit.

In exemplary embodiments the handling unit comprises a circumferential portion surrounding the opening. Advantageously, the circumferential portion defines a general plane, this allowing e.g. foil-, film- or paper-like materials to be used as sealing members. In exemplary embodiments when it is desirable to sterilize the entire first unit, the seal member may be penetratable for sterilizing gases (e.g. ethylene oxide or dry steam), yet being non-penetratable for germs. By this arrangement the first unit can serve as a packaging for the second unit, this further reducing costs as well as overall size.

In exemplary embodiments the handling unit comprises a unitary housing portion defining an interior space which in combination with the seal member provides the closed space. The housing portion may be provided by a thermo-formed or injection moulded unitary structure.

In a further aspect a device is provided, comprising a first unit and a releasably attached second unit. The first unit comprises a mounting surface adapted for application to the skin of a subject, and a transcutaneous access device (in the following also termed a transcutaneous device) comprising a distal pointed end adapted to penetrate the skin of the subject, and the second unit comprises a portion (e.g. a flange defining the general plane) adapted to engage the skin of the subject. The transcutaneous device has a first position in which the distal end is retracted relative to the skin-engaging portion and a second position in which the distal end projects relative to the skin-engaging portion. The second unit comprises actuatable driving means adapted to move the transcutaneous device from the first position to the second position when the driving means is actuated with the second unit attached to the first unit. By this arrangement the second unit can be brought in engagement with the skin of the subject where after the driving means can be actuated for insertion of the transcutaneous device. In an exemplary embodiment of this arrangement the transcutaneous device is fixedly attached to the first unit, the first unit having a first position in which the mounting surface is retracted relative to the skin-engaging portion, and a second position in which the mounting surface has been moved to a plane defined by the skin-engaging portion, whereby the mounting surface engages the skin of the user and the transcutaneous device penetrates the skin when the driving means is actuated. The first unit may be arranged in an inclined position, this allowing the infusion device to be pivoted into its second skin-contacting position in a well controlled way.

In a yet further aspect a device is provided, comprising a first unit and a releasably attached second unit. The first unit comprises a mounting surface adapted for application to the skin of a subject, and a transcutaneous device comprising a distal pointed end adapted to penetrate the skin of the subject, wherein the transcutaneous device has a first position in which the distal end is retracted relative to the mounting surface, and a second position in which the distal end projects relative to the mounting surface. The second unit comprises actuatable driving means adapted to move the transcutaneous device from the first position to the second position when the driving means is actuated with the second unit attached to the first unit. By this arrangement the first unit can be applied to the skin of the subject where after the driving means can be actuated for insertion of the transcutaneous device.

The transcutaneous device may be in the form of a pointed hollow infusion needle, a micro needle array, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle.

The first and second units may be releasably attached to each other by any suitable means allowing the device initially to be handled and applied against the skin as a unitary device, yet allowing the units to be separated by the user, e.g. by a frictional fit, releasable gripping means with or without locking means, or by breakable attachment means such as adhesives or welding. The mounting surface may be held in contact with the skin surface by use of additional means (e.g. adhesive bandages), however, preferably the mounting surface comprises adhesive means for attaching the first unit directly to the skin of the subject.

For each of the above aspects, the driving means may in the form of spring means which is arranged in an activated state when supplied to the user or can be arranged in an activated state by the user, the second unit comprising trigger means for releasably retaining the spring means in the actuated state (e.g. compressed or bend), wherein the trigger means is operable to release the spring means for moving the needle from the first position to the second position. It should be emphasized that the actuated state not necessarily is a stable state in which the spring means can be left, but a state which may require that an actuation input (e.g. a force applied by the user) is upheld, i.e. the spring means may resume an initial state if the actuation input is removed. The spring means may be any elastically compressible or deformable driving means.

When the driving means comprises spring means, the second unit may comprise actuation means actuatable from a first condition through an intermediate condition to a second condition, whereby actuation of the actuation means from the first to the intermediate condition causes activation of the driving means, and actuation of the actuation means from the intermediate to the second condition causes release of the activated spring means thereby moving the needle from the first position to the second position. By this arrangement the actuation means may serve as a user interface such that the user will not have to directly engage the spring means just as the user input may be transformed, e.g. from one type of movement to another.

Advantageously the actuation means comprises an actuating element (e.g. an element which can be gripped or actuated by the user) which is moved from a first position through an intermediate position to a second position, preferably corresponding to a substantially non-composite movement (e.g. a unidirectional linear or rotational movement, without intermediate lockable state). In an alternative arrangement actuation of the actuation means from the first through the intermediate to the second condition is accomplished by moving two actuation elements against each.

Advantageously, the handling unit comprises a housing defining the interior space, the skin-mountable unit comprising an upper portion (i.e. opposite the mounting surface) facing towards the interior space, the driving means being arranged within the interior space between the upper portion and the housing. In this configuration the housing may serve as the user interface providing the above-discussed actuation means for the driving means.

For embodiments in accordance with the above yet further aspect, the mounting surface is advantageously generally planar and arranged substantially corresponding to the general plane. When such a mounting surface comprises adhesive means for attaching the first unit to the skin of the subject, the seal member may advantageously be releasably attached to the adhesive means, this arrangement avoiding the use of a separate releasable protecting means such as a liner (e.g. a foil or sheet member) on the adhesive. In case a separate liner is provided, the liner and the seal member may be arranged such that pealing off the seal member automatically result in the liner being peeled of, this irrespective of the position of the mounting surface.

As indicated above, the present invention may be utilized in combination with a number of different types of devices.

For example, for a needle device as described above the needle may be in the form of a hollow infusion needle, the first unit further comprising a reservoir adapted to contain a liquid drug and comprising in a situation of use an outlet in fluid communication with the infusion needle, as well as expelling means for expelling a drug out of the reservoir and through the skin of the subject via the hollow needle. The reservoir and the expelling means may be of any suitable type, e.g. of any of the types described in the above-referred documents.

In a further embodiment the first unit comprises a transcutaneous device comprising a transcutaneous member (e.g. a soft cannula or a sensor) in combination with a co-axially or co-linearly arranged pointed insertion needle, the insertion needle and the transcutaneous member being arranged to be simultaneously moved by the driving means from their respective first position to their respective second position when the driving means is actuated, the insertion needle being removable from the transcutaneous member after insertion. Advantageously the insertion needle is attached to or gripped by the driving means, this allowing the insertion needle to be removed from the first unit together with the second unit.

Corresponding to the above-described aspects the insertion needle may be fixed or moveable relative to the mounting surface. The insertion needle may have any desirable configuration such as solid or grooved.

The above-described embodiments have all been provided with a transcutaneous device adapted to penetrate the skin of a subject, however, the present invention may also be used in combination with skin-mountable devices not comprising a transcutaneous device.

In a further aspect of the invention, a method of applying a device to a skin surface of a subject is provided, the method comprising the steps of: (a) providing a device having a first unit and a releasably attached second unit, wherein the first unit comprises a generally planar mounting surface comprising adhesive means for adhering the first unit to the skin of the subject. The second unit comprises an interior space accommodating the first unit and having an opening through which the first unit can be moved when detached from the second unit, the second unit having a circumferential portion defining a general plane and surrounding the opening, the mounting surface being arranged interiorly in respect of the general plane or substantially corresponding to the general plane, a seal member releasably attached to the circumferential portion, thereby providing a closed space for the first unit. The method comprises the further steps of (b) removing the seal member, (c) arranging the device in contact with the skin of the subject, and (d) removing the second unit from the first unit.

Depending on whether the mounting surface initially is positioned interiorly in respect of the general plane or substantially corresponding to the general plane, the adhesive surface may be placed in contact with the skin surface either when the device is subsequently moved towards the skin (e.g. by actuation means) or when the device is initially placed on the skin surface.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member (including an array of micro needles) adapted to penetrate the skin of a subject.

BRIEF DESCRIPTION OF THE DRAWINGS

In the following the invention will be further described with references to the drawings, wherein FIG. 2A shows in a perspective view the medical device of FIG. 1 gripped by the user corresponding to a second state of use, FIG. 2B shows the needle device of FIG. 1A with an outer portion cut away, FIG. 2C shows the first unit of the needle device of FIG. 1A.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use.

FIGS. 1-4 show in schematic representations perspective views of different states of use of a medical device in accordance with the invention. Correspondingly, the configuration of the different structures as well as there relative dimensions are intended to serve illustrative purposes only.

Figure 1:
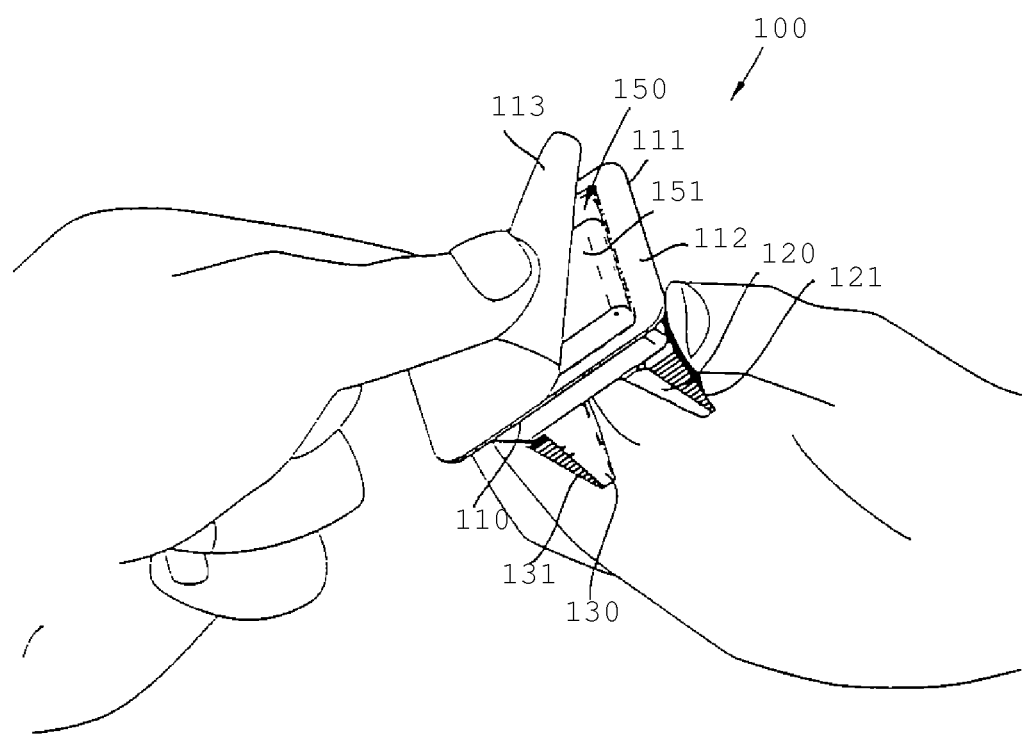
FIG. 1 shows in a perspective view a first embodiment of a medical device gripped by a user corresponding to a first state of use.

More specifically, FIG. 1 shows a first embodiment of a medical device 100 gripped by a user. The medical device comprises a second unit 110 with a housing defining an interior space 115, and a first unit 150 releasably attached within the interior space. In the following the second unit will also be termed the "inserter". The housing comprises a main portion with a lower opening surrounded by a circumferential flange 111 extending away from the housing, the flange having a lower surface 112 defining a general plane for the medical device. The housing further comprises first and second upwardly protruding actuation members (or handling members) 120, 130 arranged on the upper portion of the housing opposite the opening, the actuation members comprising ribbed portions 121, 131 allowing for easy gripping by a user, e.g. using the first and second fingers as shown. The first unit is in the form of a needle device (e.g. an infusion device or a sensor device) comprising an adhesive mounting surface 151 adapted for application to the skin of a subject, the mounting surface being generally planar and arranged substantially corresponding to the general plane. The needle device further comprises a needle (not shown) having a distal pointed end adapted to penetrate the skin of the subject, the needle having a first position in which the distal end is retracted relative to the mounting surface, and a second position in which the distal end projects relative to the mounting surface. The first position may also be termed an initial position and the second position may also be termed an advanced position.

The inserter further comprises a foil member 113 which, when supplied to the user, is attached to the circumferential lower surface of the flange 111 thereby providing a sealed cavity in which the needle device is arranged. The foil member is further releasably attached to the adhesive means arranged on the mounting surface of the needle device. When the user intends to use the needle device, the foil member is peeled away as show in FIG. 1 whereafter the medical device 100 can be placed on a skin portion of the user (see FIG. 2A), the needle device thereby adhesively engaging the skin.

Corresponding to the invention, the inserter further comprises actuatable driving means adapted to move the needle from the first position to the second position when the driving means is actuated with the second unit attached to the first unit. As best seen in FIG. 2B the driving means is in the form of an angularly bend leaf spring 140 comprising an upper portion 142 extending into the interior of the first actuation member 120 and a lower portion 141 with a distal end which in an initial state rests on a shelf member 144 protruding inwardly from the housing. In the initial state as supplied to the user, the spring is preferably in a relaxed condition and the spring may be held in place merely in cooperation with the first actuation member and the shelf, however, to prevent the spring from disengaging after actuation (see below) the upper portion may be attached to the first actuation member. The first actuation member is pivotably attached to the main portion by an integrally formed hinge 122. To prevent unintentional movement of the first actuation member and serving as tamper evidence, breakable locking means 123 is provided between the first actuation member and the main portion.

As best seen in FIG. 2C, the needle device comprises a lower base portion 155 defining the mounting surface, and an upper housing portion 156 pivotably attached to the base portion by hinge means 157. The needle is fixedly attached to the housing portion, the mounting surface comprising an opening (not shown) through which the needle can be advanced from its first to its second position when the housing portion is moved from an initial upper position to a lower engagement position. Between the two portions is arranged locking means (not shown) allowing the housing portion to be locked to the base plate when moved into engagement therewith.

Figure 3A:
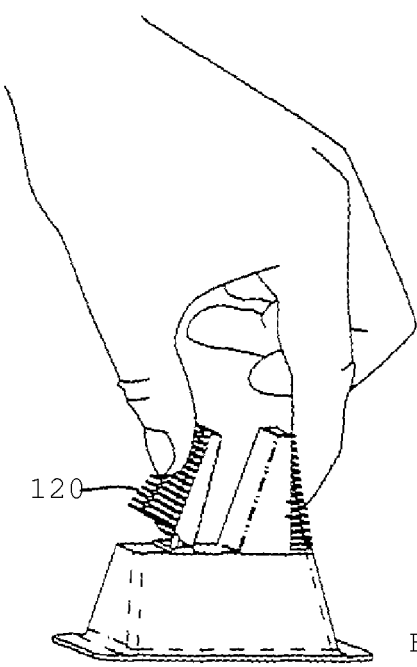
FIGS. 3A-3C shows a third state of use corresponding to FIGS. 2A-2C.
Figure 3B:
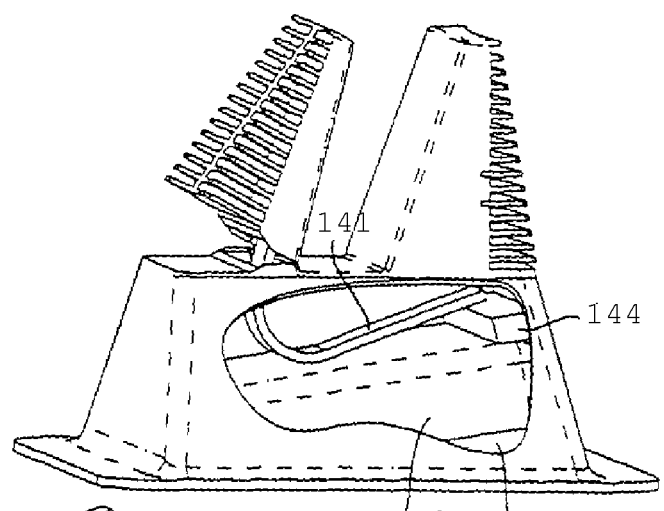

After having placed the medical device on a skin portion, the user presses the actuation members towards each other to activate the driving means, thereby breaking the locking means as shown in FIG. 3A. In an alternative embodiment (not shown) the locking means may be collapsible. During this action the first actuation member is moved from a first (initial) position (or condition) through an intermediate position to a second position, during which movement of the first actuation member from the first to the intermediate position causes activation of the spring, and actuation of the first actuation member from the intermediate to the second position causes release of the activated spring thereby moving the needle from the first position to the second position. More specifically, corresponding to the intermediate condition, the leaf spring has been bent but the lower portion 141 is still resting on the shelf 144 (see FIG. 3B) whereby energy is elastically stored in the spring. Corresponding to the second condition the spring is released from the shelf, the lower portion of the spring thereby being forced downwardly engaging the upper surface of the housing portion 156, whereby the latter is pivoted downwardly into locking engagement with the base portion 155 as shown in FIGS. 4B and 4C. During this action the needle is moved from its first to its second position, the pointed distal end thereby being introduced through the skin of the user. As seen in FIG. 3B the inserter comprises a protrusion 145 which in the initial state is in engagement with a corresponding depression on the housing portion 156 thereby serving (in combination with similar opposed means (not shown)) as a releasably attachment means between the two units.

Figure 4A:
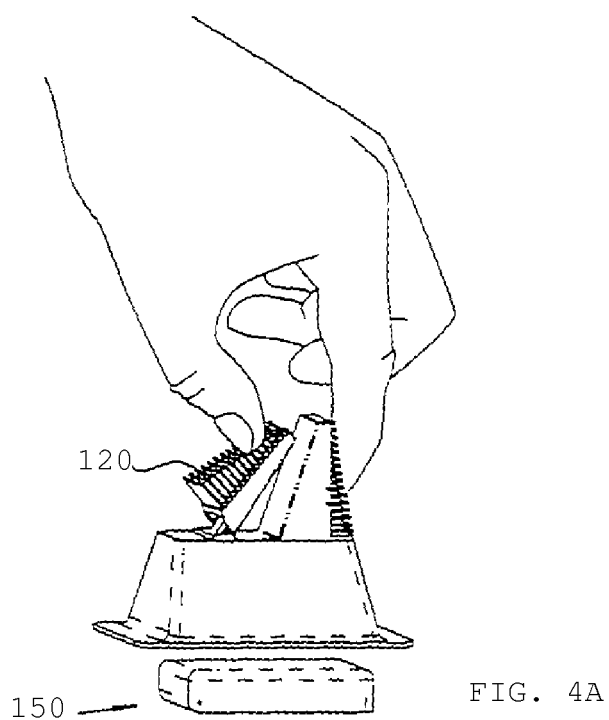
FIGS. 4A-4C shows a fourth state of use corresponding to FIGS. 2A-2C.
Figure 4B:
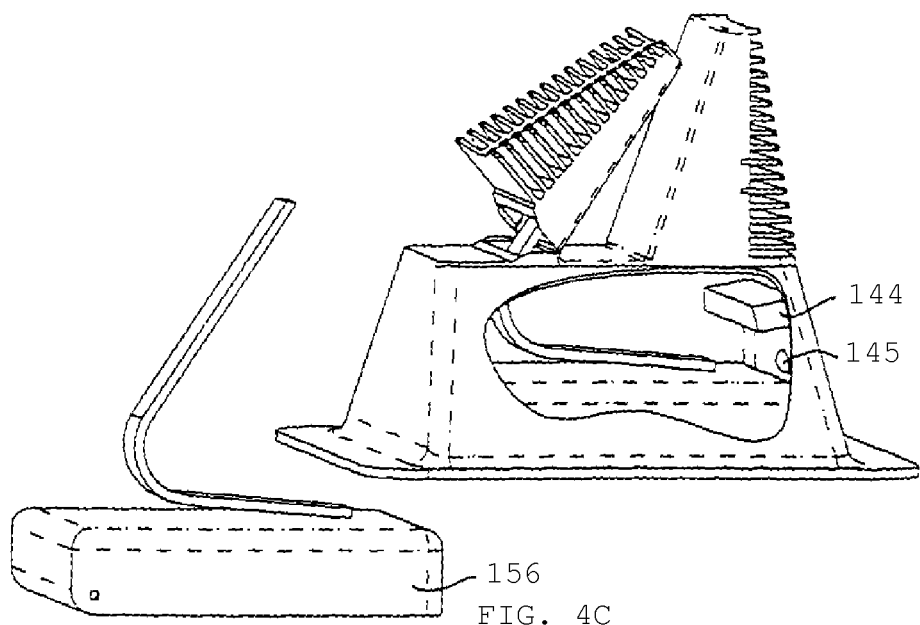
Figure 4C:
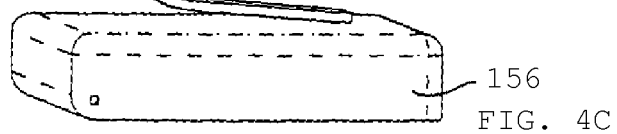
Figure 5:
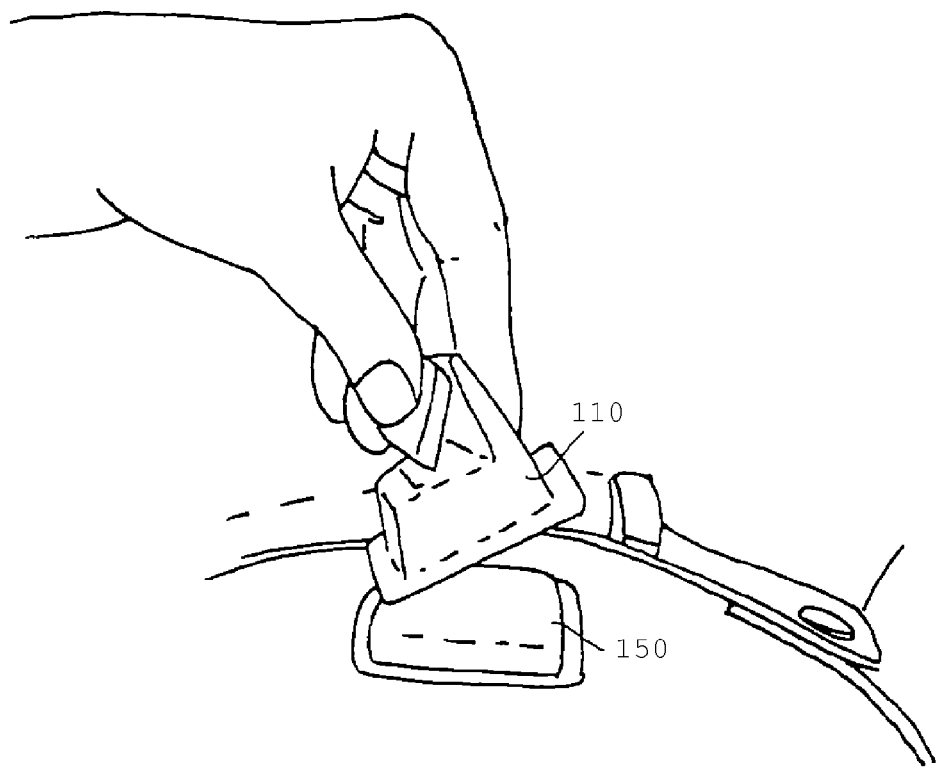
FIG. 5 shows in a perspective view the medical device of FIG. 1 gripped by the user corresponding to a fifth state of use.

When the needle has been introduced the inserter can be removed as shown in FIG. 4A. FIG. 5 shows the same situation seen from the perspective of the user when the needle device has been placed on the abdomen.

Figure 6:
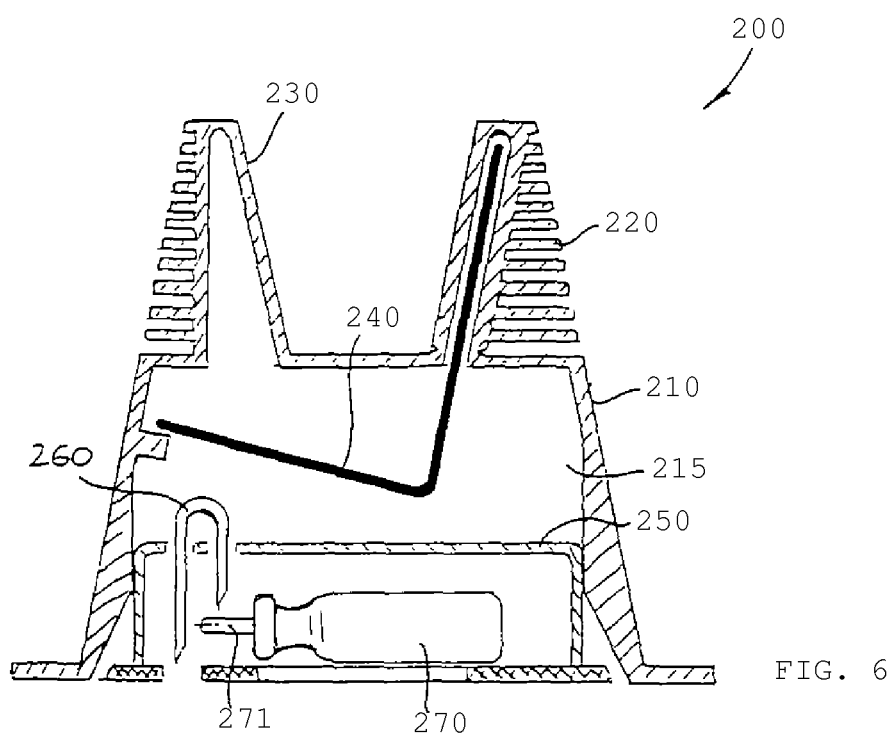
FIG. 6 shows in cross-section a second embodiment of a medical device.

In the first embodiment the needle was attached to an upper housing portion which was moveably arranged relative to the mounting surface, thereby providing the relative movement between the needle and the mounting surface. In FIG. 6 is shown a second embodiment of a medical device 200 substantially corresponding to the first embodiment, the device comprising an inserter 210, defining an interior space 215 with a leaf spring 240, frictionally coupled to an infusion device 250 comprising a hollow infusion needle 260, a drug-containing cartridge 270 as well as expelling means (not shown) arranged therewithin. However, in contrast to the first embodiment, merely the needle is moveable relative to the mounting surface. In the shown schematic embodiment the needle is bent in a U-form with the U-portion protruding through an upper surface of the infusion device, the needle further comprising a pointed distal end adapted to penetrate the skin of the user and a pointed proximal end adapted to penetrate a needle-penetratable sealing member 271 of the cartridge. In alternative embodiments the needle may be arranged within the infusion device, additional means being adapted to transfer the movement of the spring to the needle (see FIG. 9). In respect of use and actuation of the medical device, the second embodiment corresponds to the above-described first embodiment.

Figure 7:
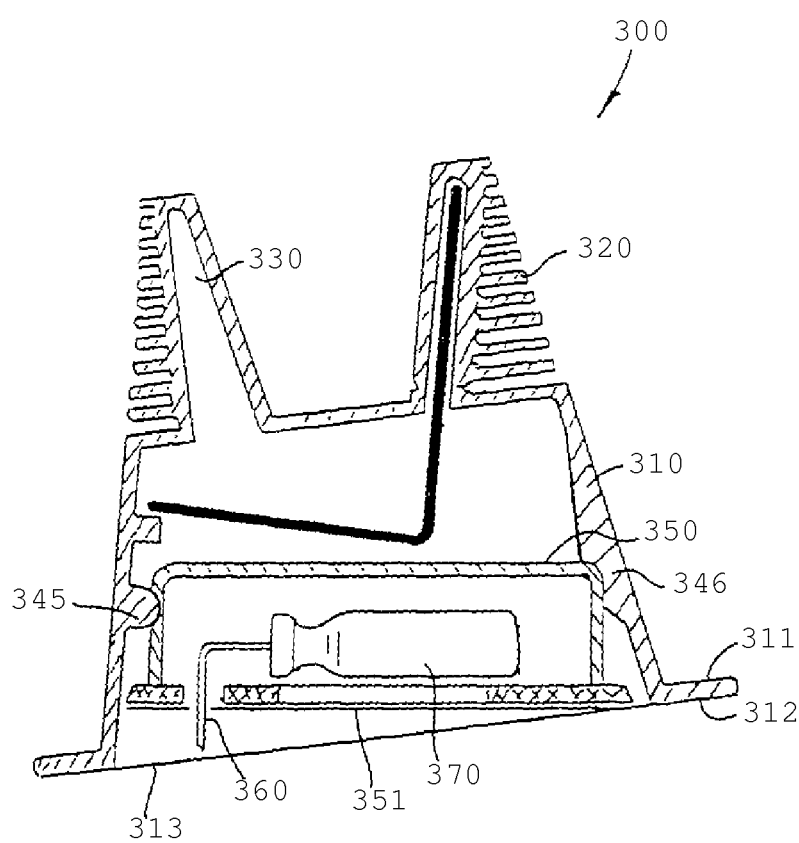
FIG. 7 shows in cross-section a third embodiment of a medical device.

In FIG. 7 is shown a third embodiment of a medical device 300 substantially corresponding to the first embodiment, the device comprising an inserter 310 coupled to an infusion device 350 comprising a hollow infusion needle 360 protruding from a mounting surface of the infusion device, a drug-containing cartridge 370 as well as expelling means (not shown) arranged therewithin. However, in contrast to the first embodiment, the mounting surface is initially arranged in a retracted position relative to the general plane defined by the lower surface 312 of the flange. As appears, the infusion device is arranged in an inclined position, this allowing the infusion device to be pivoted into its second skin-contacting position in a well controlled way. When comparing the first and third embodiment, it appears that the infusion device 350 corresponds to the upper housing portion 156, both members being arranged in an inclined position and comprising a fixedly attached needle. The inserter comprises gripping means 345, 346 in engagement with corresponding areas on the housing portion of the needle device thereby serving as a releasably attachment means between the two units.

The protruding portion of the needle is preferably supplied to the user with a protecting member (not shown). When the device is to be used, the user removes the sealing foil member 313, the protecting means, e.g. a peelable liner or foil member 351 covering the adhesive on the mounting surface as well as the needle protecting member, after which the medical device can be placed against the skin of the user corresponding to the situation shown in FIG. 2A. The liner may as shown be coupled to the foil allowing the two members to be removed in one operation. In respect of actuation of the medical device, the third embodiment substantially corresponds to the above-described first embodiment, the main difference being that the base portion (and thereby the mounting surface) initially is attached to the housing portion forming a unitary infusion device.

Figure 8:
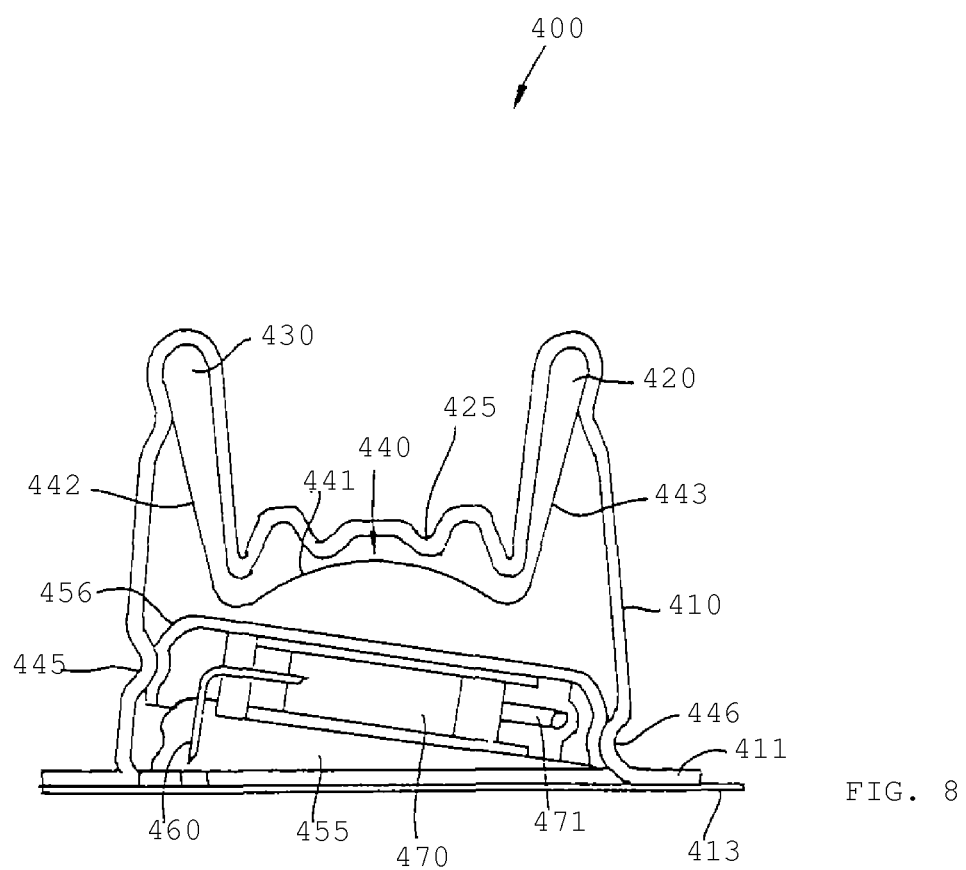
FIG. 8 shows in cross-section a fourth embodiment of a medical device.

In FIG. 8 is shown a fourth embodiment of a medical device 400 substantially corresponding to the first embodiment, the device comprising an inserter 410 coupled to an infusion device 450, the infusion device comprising a hollow infusion needle 460 mounted in an upper housing portion 456 and arranged in a retracted position relative to a base portion 455, and a drug-containing cartridge 470 proximally provided with a conduit 471 in communication with gas generating expelling means (not shown) arranged therewithin.

Whereas the inserter of the first embodiment is suitable for manufacture using injection molding, the inserter of the forth embodiment has been adapted for thermoforming, i.e. corresponding to the method often used for cost effective manufacture of packaging materials.

More specifically, the inserter comprises a lower opening surrounded by a circumferential flange 411 to which a seal member 413 is releasably attached, and two upwardly protruding substantially identical actuation members 420, 430 between which is provided a number or grooves 425 allowing the two actuation members to be pressed against each other. The inserter further comprises a first set of inwardly protruding members 445, 446 adapted to engage corresponding recesses on the infusion device, and a second set of inwardly protruding members 422, 432 adapted to hold a spring in place. The spring is in the form of a bi-staple leaf spring comprising an initially upwardly curved central portion 441 and two upwardly protruding leg portions 442, 443 arranged within the actuation members.

After having removed the seal member 413 and the liner protecting the adhesive, the medical device 400 is placed on a skin portion of the user. The user presses the two actuation members towards each other to activate the driving means. During this action the actuation members are moved from a first (initial) position (or condition) through an intermediate position to a second position, during which the spring is activated and released. More specifically, corresponding to the intermediate condition, the two leg portions have been moved towards each other thereby tensioning the curved portion of the spring, however, corresponding to the second condition the bi-stable spring suddenly transforms into its second bi-stable state whereby the curved portion is forced downwardly engaging the upper surface of the infusion device, whereby the latter is pivoted downwardly into engagement with the base portion whereby the needle is introduced through the skin of the user. As the second bi-stable state is only semi-stable, the spring will return to its initial position as the user reduces the compression force on the actuation members, however, this will not influence the infusion device. When the needle thus has been introduced the inserter can be removed.

In the above described embodiments the needle (or the member comprising the needle) has been held in its non-actuated state by frictional means or gripping means, however, in an alternative configuration additional releasable locking means (not shown) may be provided. In advantageous embodiments such locking means is coupled to the user actuatable actuation means such that the locking means is released in combination with actuation of the driving means. Such locking means may be formed as a separate member or may be formed integrally with either a housing or a spring member.

Figure 9:
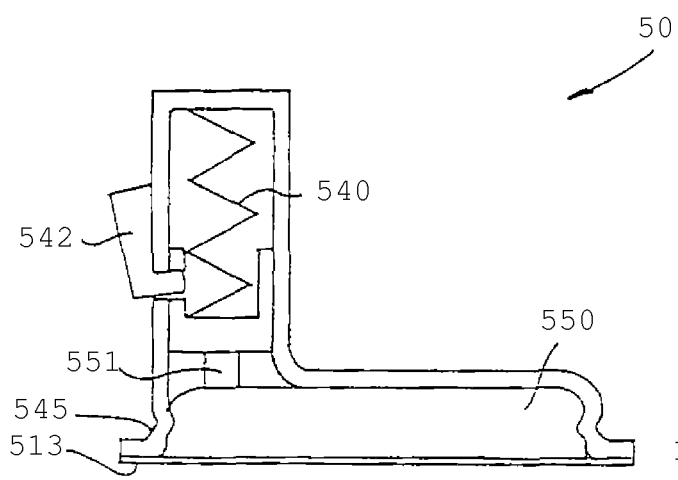
FIG. 9 shows in cross-section a fifth embodiment of a medical device.

FIG. 9 shows a fifth embodiment of a medical device 500 in which the driving means is (or can be) arrested in an activated state before being released by the user. The needle device 550 substantially corresponds to the second embodiment, i.e. merely the needle is moveable relative to the mounting surface, the needle being associated with additional transfer means 551 protruding from the upper surface of the needle device and adapted to be engaged by the drive means.

The inserter comprises a drive means in the form of a spring actuated piston assembly 540, 541 acting on the transfer means. In the shown embodiment the medical device is supplied to the user as a sealed unit with the spring in a pre-tensioned state, the inserter being provided with user actuatable release means 542 allowing the user to release the spring after the device has been placed on a skin portion of the user as discussed above. Advantageously, the release means may be designed to allow the combined device to be provided in a sterilized and sealed condition (not shown).

In an alternative embodiment (not show) the inserter may be supplied with the spring in a non-tensioned state, the inserter comprising means allowing the user to activate and lock the spring in an activated state. In a further alternative embodiment (not show) such an inserter may be supplied as a separate unit in which the needle device is mounted by the user. In this way the inserter can be provided as a durable unit.

Figure 10:
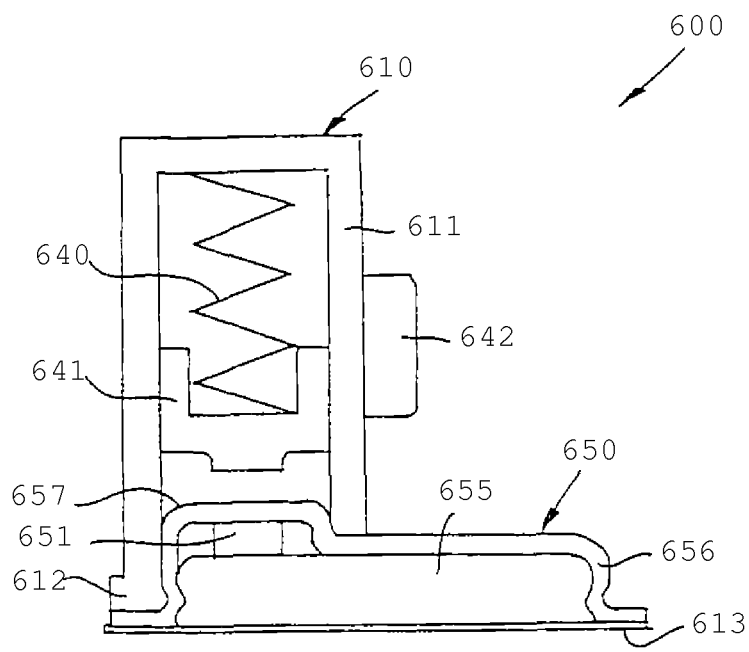
FIG. 10 shows in cross-section a sixth embodiment of a medical device.

FIG. 10 shows a sixth embodiment of a medical device 600 substantially corresponds to the fifth embodiment, however, the inserter is provided as a separate unit adapted to engage a needle device provided as a sealed unit.

More specifically, the needle device 650 resembles the combined device of the fifth embodiment (i.e. comprising a needle device and a casing therefore), however, the driving means has been omitted allowing the needle device to be supplied as a compact, sterilized and sealed unit comprising a needle device 655 and an outer housing (e.g. in the form of a closed packaging) 656, 613, the unit being adapted to be mounted in a separate inserter 610. The inserter comprises a housing 611 adapted to engage the outer housing of the needle device and comprises a drive means 640, 641, 642 corresponding to the fifth embodiment, i.e. a lockable, spring-driven piston adapted to engage the transfer means 651 through a deformable portion 657 of the outer housing. The two units may be provided with releasable gripping means 612 allowing the inserter to be attached to the needle device prior to arranging the needle device on a skin portion, this improving handling. Correspondingly, the user may place the needle device 650 in the inserter before removing the protective foil 613. The inserter may be supplied separately as a durable unit or it may be supplied as part of a kit, e.g. a package containing a plurality of needle devices and an inserter. Indeed, the transfer means may also be actuated manually by the user by simply applying pressure with a finger.

In the above-described embodiments a medical device has been described comprising a reservoir, however, for better illustrating the principles of the present invention, the means for expelling a drug from the reservoir has been omitted in the figures. Such expelling means, which as the reservoir does not form part of the present invention in its basic form, may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 11A:
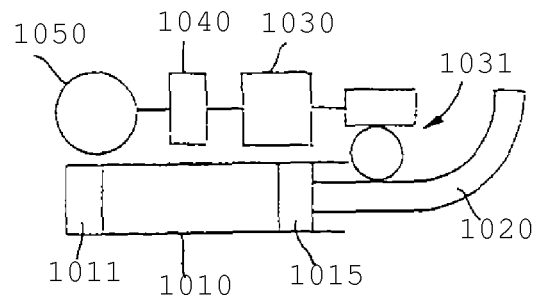
FIGS. 11A-11D shows different expelling means suitable for use with the invention.

In FIGS. 11A-11D examples of expelling means suitable for use with the present invention are shown schematically, however, these are merely examples. More specifically, FIG. 11A shows a pump arrangement comprising a drug-containing cartridge 1010 having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 11B:
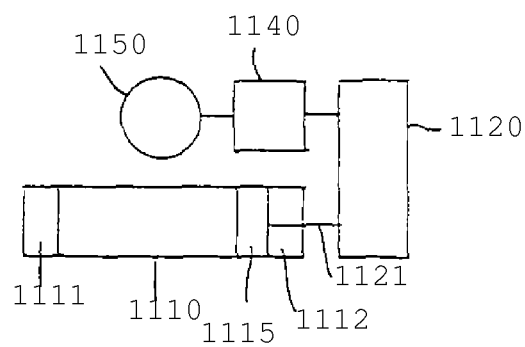

FIG. 11B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 11C:
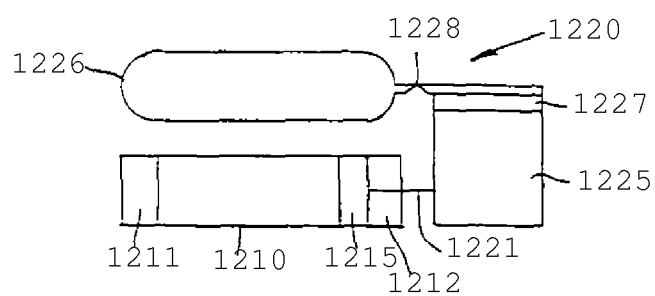

FIG. 11C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semipermeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 11D:
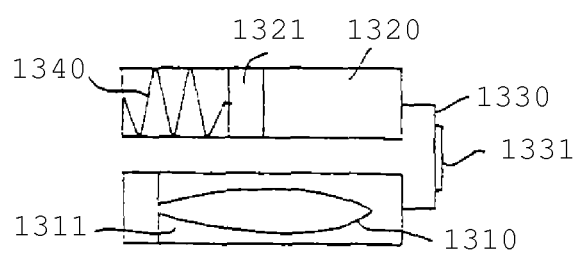

FIG. 11D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

In the above described embodiments, the transcutaneous device has been in the form of a unitary needle device (e.g. an infusion needle or a needle sensor), however, a transcutaneous device may also be introduced subcutaneously as a combination of transcutaneous member and an insertion needle which is withdrawn fully or partly after insertion thereof.

Figure 13A:
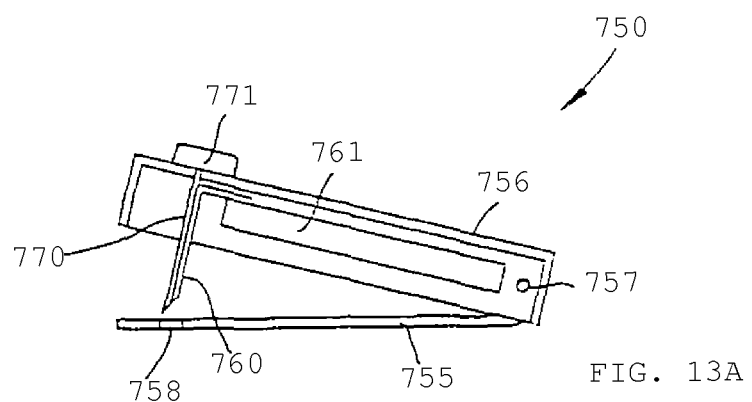
FIGS. 13A-13C shows different states of use for a sensor device.
Figure 13B:
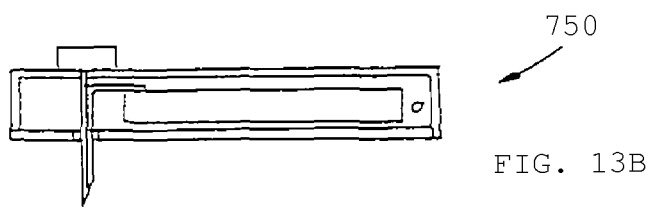
Figure 13C:
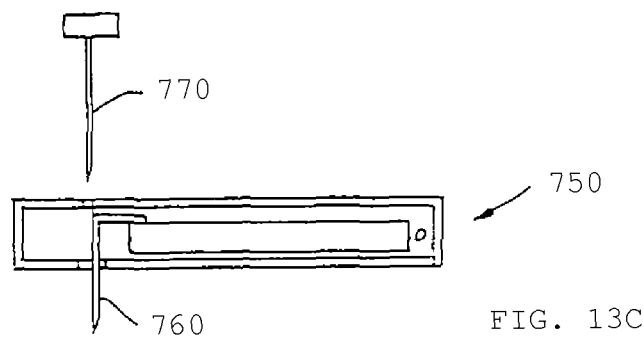

With reference to FIGS. 13A-13C an embodiment of a sensor device will be described, having the same general hinged configuration as the needle device of the first embodiment, wherein the transcutaneous device is in the form of a combined needle sensor and corresponding insertion needle therefore. For improved clarity, the structures relating to the inserter have been omitted in the drawings.

More specifically, the sensor device 750 comprises a lower base portion 755 defining the mounting surface, and an upper housing portion 756 pivotably attached to the base portion by hinge means 757. A relatively flexible needle-formed sensor 760 with a distal sensor element is fixedly attached to the housing portion and is in communication with signal receiving means 761. The signal receiving means may be contact means for connecting the sensor device to external processor means for evaluating the signals, transmitting means for wireless transmission to an external processor, or a processor arranged within the housing. The needle-sensor is supported by an insertion needle 770, the support preventing deformation of the needle-sensor during insertion. The insertion needle is slidably received in the upper housing portion and comprises a gripping member 771 allowing the insertion needle to be withdrawn by the user after insertion has taken place. The mounting surface comprises an opening 758 through which the two needles can be advanced from its first to its second position when the housing portion is moved from an initial upper position to a lower engagement position. Between the two portions is arranged locking means (not shown) allowing the housing portion to be locked to the base plate when moved into engagement therewith.

FIG. 13A shows the sensor device in an initial position, FIG. 13B shows the sensor device after the two needles 760, 770 have been introduced and the inserter has been removed, and FIG. 13C shows the situation in which the needle-sensor has been inserted and the insertion needle has been withdrawn. In the shown embodiment the insertion needle is adapted to be withdrawn by the user, however, the driving means and the gripping means may be designed to engage each other such that the insertion needle is removed from the sensor device together with the inserter.

Figure 3C:
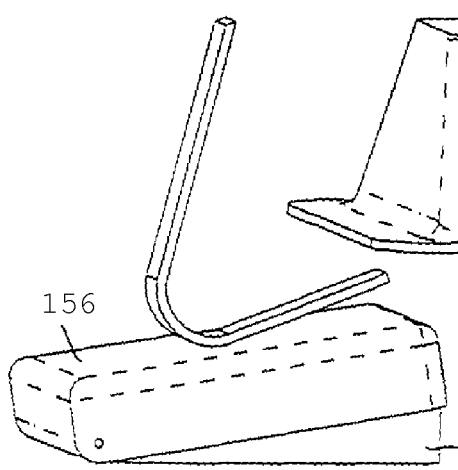
Figure 14A:
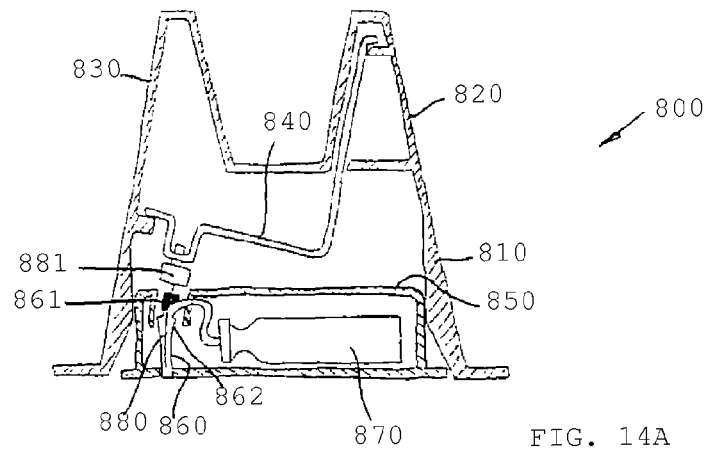
FIGS. 14A-14C show in cross-sections a further embodiment of a medical device.
Figure 14B:
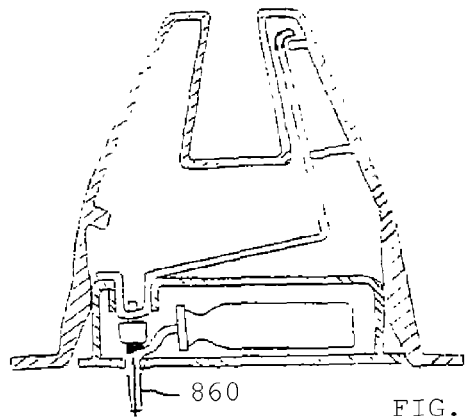
Figure 14C:
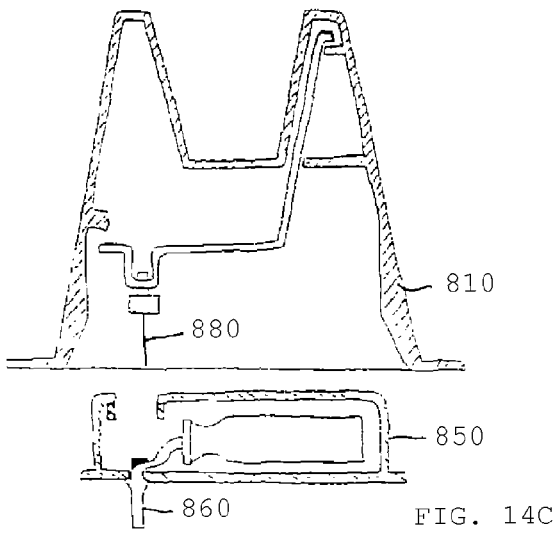

In FIG. 14A is shown a schematic representation of a further embodiment of a medical device 800 substantially corresponding to the embodiment shown in FIG. 7, the device comprising an inserter 810 coupled to an infusion device 850 comprising a flexible infusion cannula 860 adapted to cooperate with a pointed insertion needle 880 mounted on the leaf spring 840 by means of a needle carrier 881, a drug-containing cartridge 870 as well as expelling means (not shown) arranged there within. The flexible cannula (which e.g. may be of the soft "Teflon®" type) comprises a self-sealing needle-penetratable septum portion 861 through which the insertion needle is mounted as well a circumferentially arranged locking means in form of a collar 862. In the initial position the pointed distal end of the insertion needle is arranged in a slightly retracted position relative to the distal opening of the infusion cannula and with the needle carrier positioned a small distance above the septum. When the inserter is actuated as shown in FIGS. 2-4, the needle carrier is moved downwardly thereby engaging the septum, in which position the insertion needle projects a small distance out through the cannula, and further forcing the cannula from its retracted to its extended position, the projecting pointed needle end allowing the cannula to be introduced through the skin of a subject, see FIG. 14B. In this position the locking means engages the housing of the medical device allowing the insertion needle to be removed from the device together with the inserter as seen in FIG. 14C.

In an alternative embodiment (not shown) the needle device is in the form of a so-called infusion set comprising an infusion cannula and a therethrough arranged removable insertion needle, such infusion sets typically being used to provide an infusion site in combination with (durable) infusion pumps.

In the above-described embodiments the needle has been arranged primarily for actuation by external driving means positioned above the needle device, however, with reference to FIGS. 12A-12G a drug infusion device is shown which is adapted for manual actuation by moving an actuation member in parallel with the mounting surface, such a device advantageously being supplied to the user in a sealed package in accordance with the present invention.

More specifically, a drug infusion device 901 comprises a base plate 910, a first cover member 920 and a second cover member 930, the three elements in combination forming a housing in which a pump assembly 940 and a flexible drug reservoir 950 are arranged.

The base plate comprises a lower generally planar surface 918 serving as a mounting surface comprising adhesive means for adhering the unit to the skin of a subject, and an upper surface 919 provided with connecting means allowing the first and second cover members as well as a pump assembly 940 to be mounted on the base plate. More specifically, the base plate comprises three upstanding hook-members 911 adapted to engage corresponding hook structures 921 on the first cover member to thereby lock the two members to each other in a snap-action manner, as well as a pair of parallely arranged opposed members 912 having outwardly open grooves adapted to engage corresponding flange structures 931 on the second cover member allowing the two members to be mounted in sliding engagement with each other. In order to control movement between the two members, the grooves and the flanges may be provided with corresponding ratchet or locking means 916, 932. To help align the second cover member as it is moved towards the first cover member, the base plate comprises a ridge member 913 adapted to engage a corresponding groove structure 933 on the second cover member. The base plate member further comprises an aperture 914, a part-cylindrical "female" hinge member 915 adapted to engage the pump assembly, as well as an opening 917 associated with the hinge member.

The pump assembly 940 comprises a membrane pump as well as control means, actuating means (e.g. heating means), contact means and an energy source for driving the pump. The pump assembly is configured with a (part) cylindrical hinge body 941 from which protrudes a pump body 942 wherein the pump and driving means are arranged. On the lower surface of the hinge body an engagement member 947 is arranged. The pump inlet is in fluid communication with an inlet needle 943 protruding axially from an end of the hinge body and the pump outlet is in fluid communication with an infusion needle 944 protruding from a lower surface 948 of the pump body, both needles having a pointed free end. The hinge body is adapted to be pivotally received in the hinge member 915 with the engagement member 947 arranged in the opening 917 to prevent axial displacement of the pump assembly, and with the infusion needle in alignment with the aperture 914.

The flexible reservoir 950 is in the form of a pouch- or bag-like member formed from a pliable material and provided with a needle penetratable connecting means, e.g. a self-sealing septum (not shown). The reservoir is easily collapsible allowing the drug contained therein to be sucked out by the pump without the need for additional venting means. The reservoir is mounted and hold in place under the second cover member by appropriate means. In the shown embodiment the reservoir is prefilled with a drug such as insulin, however, the reservoir may also be adapted to be filled by the user prior to user.

The above-described components are assembled in two subassemblies (see FIGS. 12C and 12D), a main assembly 960 and a reservoir assembly 970, this allowing the assemblies to be sterilized independently if necessary. More specifically, the main assembly comprises the base plate member with the first housing member mounted on top thereof providing a cavity in which the pump assembly 940 is pivotally arranged in the hinge member 915, and the reservoir assembly comprises the second housing member with the reservoir mounted corresponding to a lower surface thereof. The hinge may be configured to provide an upwardly biasing force preventing the pump assembly from pivoting downwardly. The second housing member is provided with an end portion having a grooved area 934 and an oppositely arranged shroud portion 935 adapted to slide under the first cover member, as well as a lower ramp member 936 associated with the lower surface of the second housing member, the function of which will be explained in greater detail below. The grooved area may in combination with an opposed protruding ridge 923 on the first cover member serve as engagement means allowing the infusion device to be releasable locked to corresponding engagement means on the housing member of the package (see FIG. 12G).

Figure 12A:
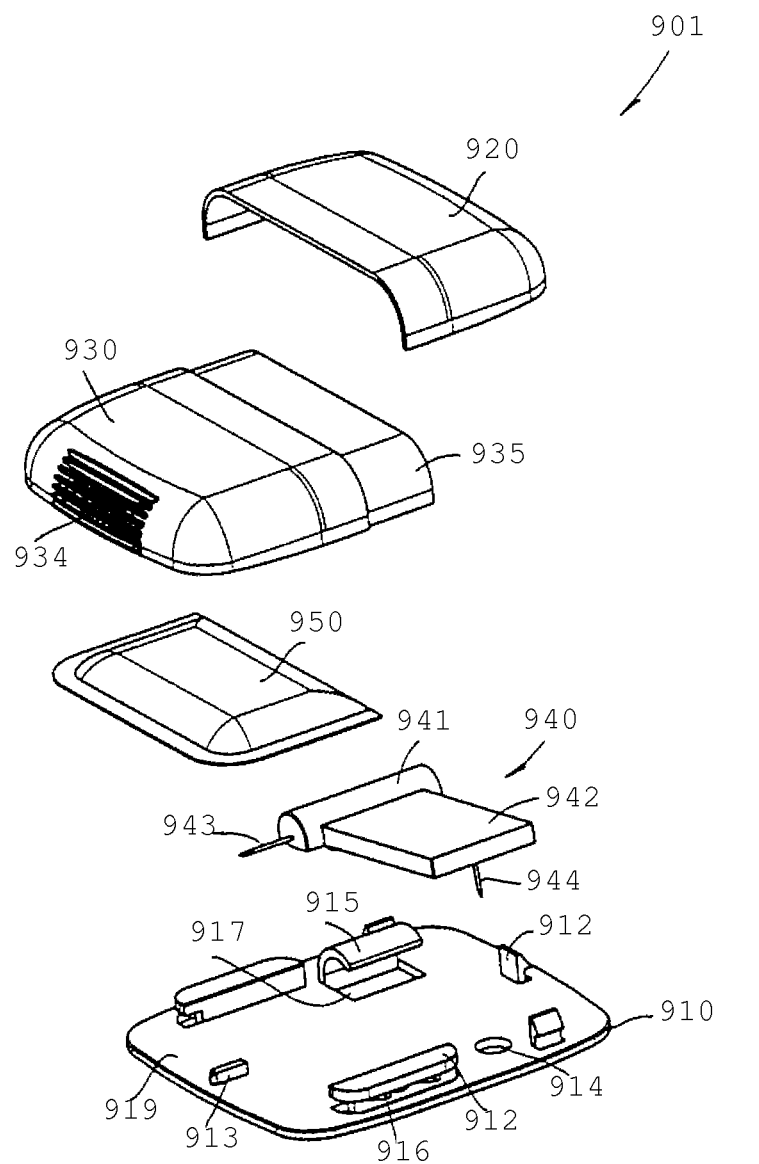
FIG. 12A shows an exploded view of a drug infusion device seen from above.
Figure 12B:
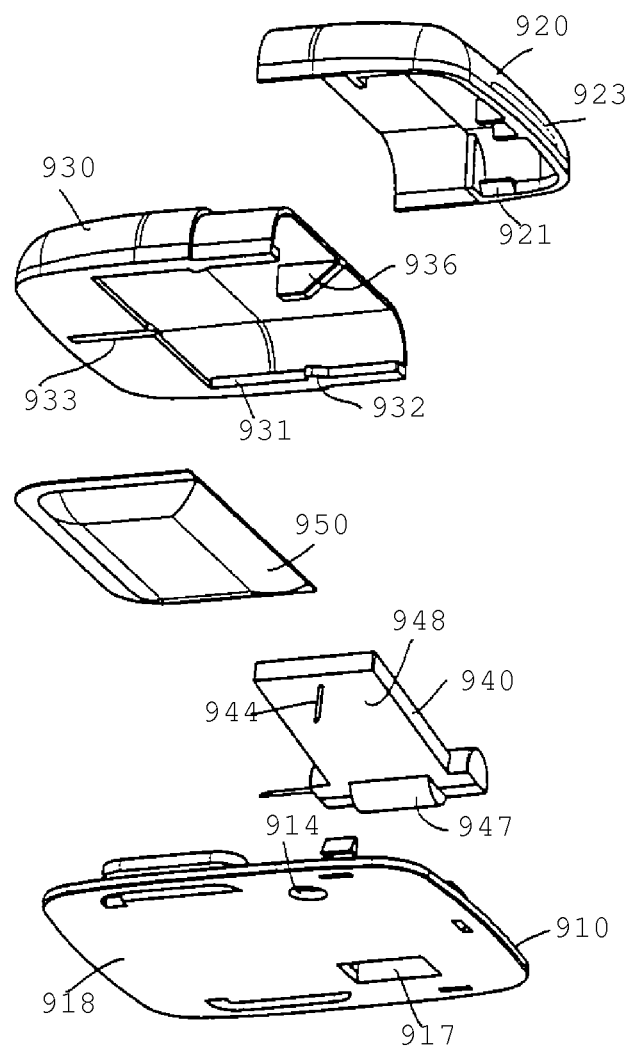
FIG. 12B shows an exploded view of the infusion device seen of FIG. 12A from below.
Figure 12C:
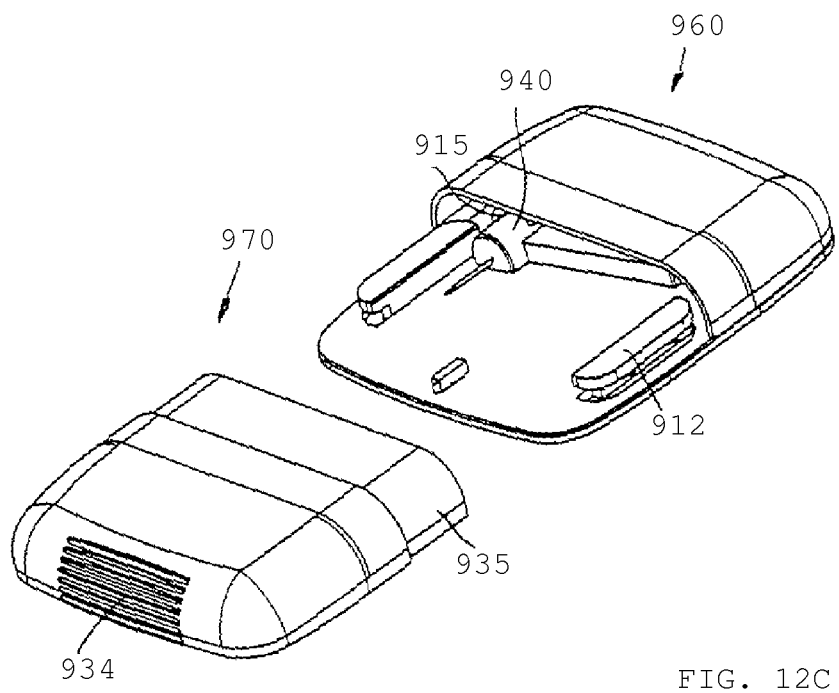
FIGS. 12C and 12D shows the infusion device comprising two sub-assemblies.
Figure 12D:
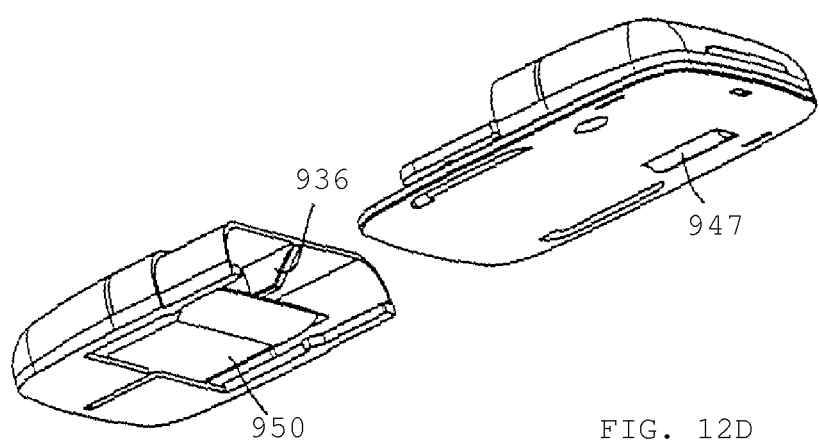
Figure 12E:
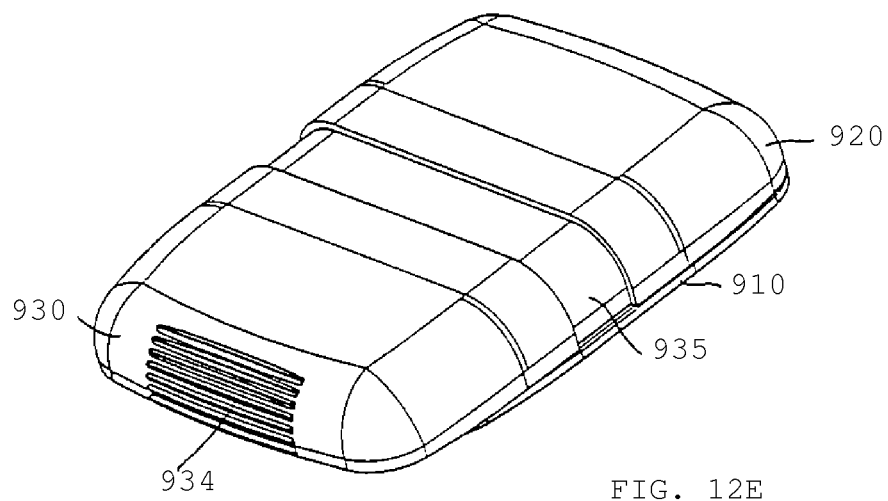
FIG. 12E shows the infusion device in an assembled initial state.
Figure 12F:
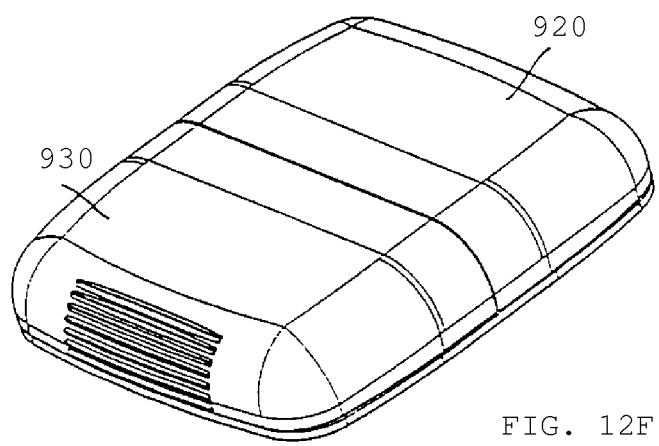
FIG. 12F shows the infusion device in an assembled actuated state.

The drug infusion device 901 is supplied to the user with the two subassemblies assembled corresponding to an initial state as shown in FIG. 12E. More specifically, the reservoir assembly is mounted in sliding engagement with the base plate member by means of the connecting members 912, 931, a cavity inclosing the reservoir thereby being formed between the second cover member and the base plate member, the reservoir connecting means being arranged in axial alignment with the inlet needle. In the initial state the reservoir assembly is not fully moved towards the first cover member, however, the shroud is partially inserted under the first cover member, this providing a closed cavity. The locking or ratchet means 916, 932 arranged between the second cover member and the base plate member may be configured to prevent that the reservoir assembly can be removed by the user.

Figure 12G:
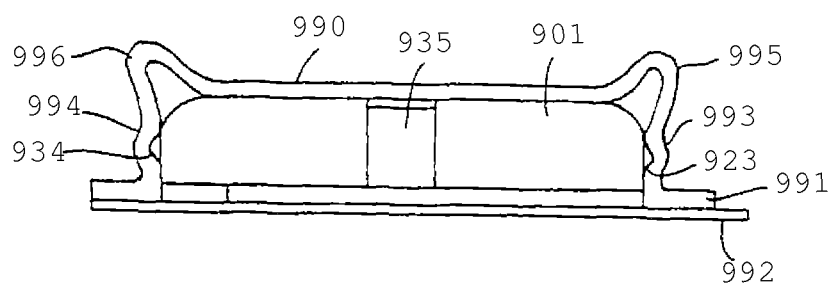
FIG. 12G shows the infusion device in its delivery package.

In accordance with the invention and as shown in FIG. 12G, the infusion device 901 is supplied in an enclosure allowing for easy handling. More specifically, the device is supplied in a package housing 990 substantially corresponding to the external configuration and size of the device in its initial state, the package housing having engagement means 993, 994 cooperating with corresponding engagement means (shown simplified) on the infusion device, and a circumferential flange 991 defining an opening substantially corresponding to the mounting surface of the device, the opening being closed by a seal member 992 releasable attached to the flange and the adhesive on the mounting surface. To improve handling the package housing comprises opposed raised portions 995, 996 allowing the container to be easily gripped by two fingers. The package housing is made from a flexible, easily deformable material.

To activate the infusion device, the reservoir assembly is moved towards the pump assembly (see FIG. 12F) whereby a number of actions takes place. More specifically, the inlet needle 943 will penetrate the reservoir connecting means providing fluid communication between the reservoir and the pump, and the ramp 936 on the second cover member will engage the pump assembly to thereby pivot it downwardly whereby the infusion needle 944 will be moved through the aperture 914. At the same time contact means arranged on the pump assembly (e.g. on the lower surface of the pump body) will be activated, thereby activating the pump control means and eventually the pump, however, the activated control means may be adapted to "wait" for a command signal from an external signal (e.g. supplied from a remote control device) before the pump is actuated. In an alternative embodiment (not shown) the reservoir assembly and the pump assembly may be adapted to move linearly, e.g. in a co-linear fashion when arranged in a "stack". In further alternative embodiments (not shown) the reservoir may be connected to the pump, the pump being started, and the needle introduced partly or fully independently of each other, e.g. by two or three user actuated actions.

The drug infusion device 901 may be used in the following way. After the seal member (and eventually a separate liner) has been removed the device in its package housing is placed on a suitable skin portion of the user, e.g. in the abdominal region. Hereafter the user presses the raised portions of the package container against each other thereby pushing the reservoir assembly serving as a button (indicated by the grooved area 934) towards the main portion until it locks in place, this, as described above, resulting in activation of the pump and introduction of the needle through the skin of the user. At the same time the package housing will disengage from the infusion device. Depending on the programming of the control means, the pump may start to operate immediately or it may wait for user activated commands before pump action is initiated, e.g. commands received from a remote commander or from input means arranged on the device.

When the device is to be removed, it may be pulled of the skin in its active state with the needle protruding from the lower surface, or the device may be reversed to its initial state before it is removed. For example, if locking means are arranged between the shroud and the first cover member, the locking means may be released by pushing down the upper surface of the first cover member.

The above-described embodiments have all been provided with a subcutaneous device adapted to penetrate the skin of a subject, however, the present invention may also be used in combination with skin-mountable devices not comprising a needle or any other skin-piercing element.

For example, the skin-mountable device may be in the form of a sensor device comprising a sensor means adapted to be arranged in contact with a skin portion of a subject and capable of being influenced by a body substance or condition and producing a signal corresponding thereto. The sensor device further comprising control means adapted to receive signals from the sensor means and generate command signals in response thereto. The control means may be adapted for connecting the sensor device to external processor means for evaluating the signals, transmitting means for wireless transmission to an external processor, or a processor arranged within the housing.

In a further embodiment the skin-mountable device is a signal device comprising first and second electrodes arranged on the mounting surface and adapted to be mounted in conductive contact with the skin of a subject, the first and second electrodes providing a pair of electrodes, and a voltage source for providing a voltage between the pair of electrodes. The signal device further comprises control means for controlling the voltage applied between the pair of electrodes, the control means being adapted for identifying a predefined condition or a signal and applying a voltage between the pair of electrodes in response thereto. Such a signal device may be provided in combination with any skin-mountable device, or it may be provided as a separate skin-mountable signal unit adapted to be in communication with and/or controlled by one or more primary devices. When provided with means for receiving externally generated (cordless) command signals, the signal device may be used in combination with devices or systems which then do not have to be skin mounted. For example, such a signal device may be utilized with a separate infusion pump which may then be carried in a belt or in a pocket. In a different technical field, people with impaired hearing may use the signal device as a hearing aid, e.g. to help hear the phone ring, an alarm clock sound or any other traditionally audible signal. Indeed, for any given combination of the signal device of the invention and an external device, the two devices will have to be adapted to communicate with each other.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

CITED DOCUMENTS WHICH ARE
INCORPORATED BY REFERENCE

U.S. Pat. No. 4,340,048
U.S. Pat. No. 4,552,561
U.S. Pat. No. 5,858,001
U.S. Pat. No. 6,280,148
U.S. Pat. No. 5,957,895
U.S. Pat. No. 5,527,288
U.S. Pat. No. 2,605,765
U.S. Pat. No. 4,340,048
EP 1 177 802
U.S. Pat. No. 5,814,020
U.S. Pat. No. 5,931,814
WO 02/15965
U.S. Pat. No. 5,482,473
U.S. Pat. No. 5,390,671
U.S. Pat. No. 5,391,950
U.S. Pat. No. 5,568,806
U.S. Pat. No. 5,954,643

The invention claimed is:

1. A device comprising:
   a skin-mountable unit having a mounting surface comprising an adhesive for adhering the unit to the skin of a subject, the adhesive being covered by a releasably attached seal member,
   a handling unit releasably attached to the skin-mountable unit in a manner that allows the handling unit to be released from the skin mountable unit after the skin-mountable unit is attached to the skin of the subject and wherein the handling unit comprises an interior space at least partially accommodating the skin-mountable unit and having an opening through which the skin-mountable unit can be moved when detached from the handling unit, the handling unit having a portion surrounding the opening, and
   the seal member being releasably attached to the surrounding portion, thereby providing a closed space for the skin-mountable unit,
   wherein the handling unit and skin-mountable unit are arranged in a releasably attached manner that allows the device to be handled and initially applied against the skin as a unitary device and wherein in situation of use the handling unit is used to aid in attaching the device to the skin.

2. A device as defined in claim 1, wherein the handling unit comprises a circumferential portion surrounding the opening.

3. A device as defined in claim 2, wherein the circumferential portion defines a general plane.

4. A device as defined in claim 3, wherein the mounting surface is generally planar and arranged substantially corresponding to the general plane defined by the surrounding portion of the handling unit.

5. A device as defined in claim 4, wherein the mounting surface is arranged in a retracted position relative to the general plane.

6. A device as defined in claim 1, further comprising a protective cover disposed between the seal member and the adhesive, wherein the seal member is connected to the protective cover.

7. A device as defined in claim 6 wherein removal of the seal member results in automatic removal of the protective cover.

8. A device as defined in claim 1, wherein the skin-mountable unit further comprising a transcutaneous device having a distal pointed end configured to penetrate the skin of the subject, the transcutaneous device having a first position in which the distal end is retracted relative to the mounting surface, and a second position in which the distal end projects relative to the mounting surface.

9. A device as defined in claim 8, further comprising an actuatable driver associated with the handling unit and configured to move the transcutaneous device from the first position to the second position when the driver is actuated with the handling unit attached to the skin-mountable unit.

10. A device as defined in claim 9, wherein the driver comprises a spring, the handling unit further comprising:
   an actuator that is actuatable from a first condition through an intermediate condition to a second condition in which the transcutaneous device is moved to its second position,
   whereby actuation of the actuator from the first to the intermediate condition causes activation of the driver, and actuation of the actuator from the intermediate to the second condition causes release of the activated spring, moving the transcutaneous device from the first position to the second position.

11. A device as defined in claim 10, wherein the actuator comprises an actuating element which is moved from a first position through an intermediate position to a second position, preferably corresponding to a substantially non-composite movement.

12. A device as defined in claim 10, wherein actuation of the actuator from the first through the intermediate to the second condition is accomplished by moving two actuation elements against each other.

13. A device as defined in claim 9, wherein the driver can be locked in its activated state.

14. A device as defined in claim 9, wherein the driver comprises a spring which is or can be arranged in an activated state, the second unit comprising a trigger for releasably retaining the spring in the actuated state, the trigger being operable to release the spring for moving the transcutaneous device from the first position to the second position.

15. A device as defined in claim 9, wherein the handling unit comprises a housing defining the interior space, the skin-mountable unit comprising an upper portion facing towards the interior space, the driver being arranged within the interior space between the upper portion and the housing.

16. A medical device as defined in claim 9, wherein the transcutaneous device is a cannula in combination with a pointed insertion needle accommodated at least partially within the cannula, the cannula having a distal opening,
   the cannula and insertion needle being arranged to be simultaneously moved by the driver from their respective first position to their respective second position when the driver is actuated,
   wherein the insertion needle is arranged to be moveable away from the distal opening when the cannula and the insertion needle have been moved to their second position.

17. A medical device as defined in claim 16, wherein the cannula comprises a needle-penetratable septum through which the insertion needle is arranged when the cannula and the insertion needle is moved from their respective first position to their respective second position.

18. A medical device as defined claim 16, wherein the insertion needle in its second position is attached to the second unit, whereby removal of the second unit from the first unit withdraws the insertion needle therefrom.

19. A medical device as defined claim 9, wherein the transcutaneous device is a longitudinal sensor device in combination with a pointed insertion needle arranged to support a distal portion of the sensor device,
   the sensor device and insertion needle being arranged to be simultaneously moved by the driver from their respective first position to their respective second position when the driver is actuated,
   wherein the insertion needle is arranged to be moveable away from the distal portion when the sensor device and the insertion needle have been moved to their second position.

20. A device as defined in claim 8 in combination with an inserter, the inserter comprising:
   a housing configured to releasably receive and support the handling unit,
   an actuatable driver,
   the handling unit comprising a portion moveable by the driver when the latter is actuated, the moveable portion of the handling unit being arranged to engage the skin-mountable unit to thereby move the transcutaneous device from its first to its second position.

21. A device as defined in claim 8, wherein the transcutaneous device is a hollow infusion needle, the skin-mountable unit further comprising:
   a reservoir configured to contain a liquid drug and comprising in a situation of use an outlet in fluid communication with the infusion needle, and
   an expelling unit configured to expel a drug out of the reservoir and through the skin of the subject via the infusion needle.

* * * * *